United States Patent [19]
Ray et al.

[11] Patent Number: 6,132,465
[45] Date of Patent: Oct. 17, 2000

[54] TAPERED PROSTHETIC SPINAL DISC NUCLEUS

[75] Inventors: Charles D. Ray, Williamsburg, Va.; Robert L. Assell, Mendota Heights, Minn.

[73] Assignee: Raymedica, Inc., Bloomington, Minn.

[21] Appl. No.: 09/090,820

[22] Filed: Jun. 4, 1998

[51] Int. Cl.[7] ................................................. A61F 2/44
[52] U.S. Cl. ........................................................ 623/17.16
[58] Field of Search ............................ 623/17.11–17.16, 623/18.11; 606/60, 61

[56] References Cited

U.S. PATENT DOCUMENTS

| | | | |
|---|---|---|---|
| 3,867,728 | 2/1975 | Stubstad et al. | 3/1 |
| 3,875,595 | 4/1975 | Froning | 3/1 |
| 3,883,902 | 5/1975 | Lynch | 3/36 |
| 4,349,921 | 9/1982 | Kuntz | 3/1 |
| 4,772,287 | 9/1988 | Ray et al. | 623/17 |
| 4,863,477 | 9/1989 | Monson | 623/17 |
| 4,904,260 | 2/1990 | Ray et al. | 623/17 |
| 4,911,718 | 3/1990 | Lee et al. | 623/17 |
| 5,047,055 | 9/1991 | Bao et al. | 623/17 |
| 5,171,280 | 12/1992 | Baumgartner | 623/17 |
| 5,192,326 | 3/1993 | Bao et al. | 623/17 |
| 5,306,309 | 4/1994 | Wagner et al. | 623/17 |
| 5,314,478 | 5/1994 | Oka et al. | 623/18 |
| 5,443,514 | 8/1995 | Steffee | 623/17 |
| 5,458,642 | 10/1995 | Beer et al. | 623/17 |
| 5,458,643 | 10/1995 | Oka et al. | 623/18 |
| 5,514,180 | 5/1996 | Heggeness et al. | 623/17 |
| 5,534,028 | 7/1996 | Bao et al. | 623/17 |
| 5,534,030 | 7/1996 | Navarro et al. | 623/17 |
| 5,571,189 | 11/1996 | Kuslich | 623/17 |
| 5,645,597 | 7/1997 | Krapiva | 623/17 |
| 5,653,762 | 8/1997 | Pisharodi | 623/17 |
| 5,674,295 | 10/1997 | Ray et al. | 623/17 |
| 5,705,780 | 1/1998 | Bao | 204/157.15 |
| 5,824,093 | 10/1998 | Ray et al. | 623/17 |

FOREIGN PATENT DOCUMENTS 2 639 823-A1  8/1990  France .............................. A61F 2/44

OTHER PUBLICATIONS

Article entitled, The Artificial Disc Introduction, History and Socioeconomics, by Charles Dean Ray; pp. 205–225; dated 1992.

*Primary Examiner*—V. Millin
*Assistant Examiner*—Tram A. Nguyen
*Attorney, Agent, or Firm*—Dicke, Billig & Czaja, P.A.

[57] ABSTRACT

A wedge-shaped prosthetic spinal disc nucleus including a hydrogel core surrounded by a constraining jacket. The hydrogel core is preshaped to form the wedge shape in a hydrated state. The constraining jacket is flexible, but substantially inelastic and is configured to prevent the hydrogel core from conforming to an anulus upon hydration. The prosthetic spinal disc nucleus corresponds generally to anatomical variations in disc space geometry, generally defined by separable areas or compartments, thus improving performance. In one preferred embodiment, the prosthetic spinal disc nucleus includes a radiopaque marker for indicating a location and orientation following implant.

29 Claims, 7 Drawing Sheets

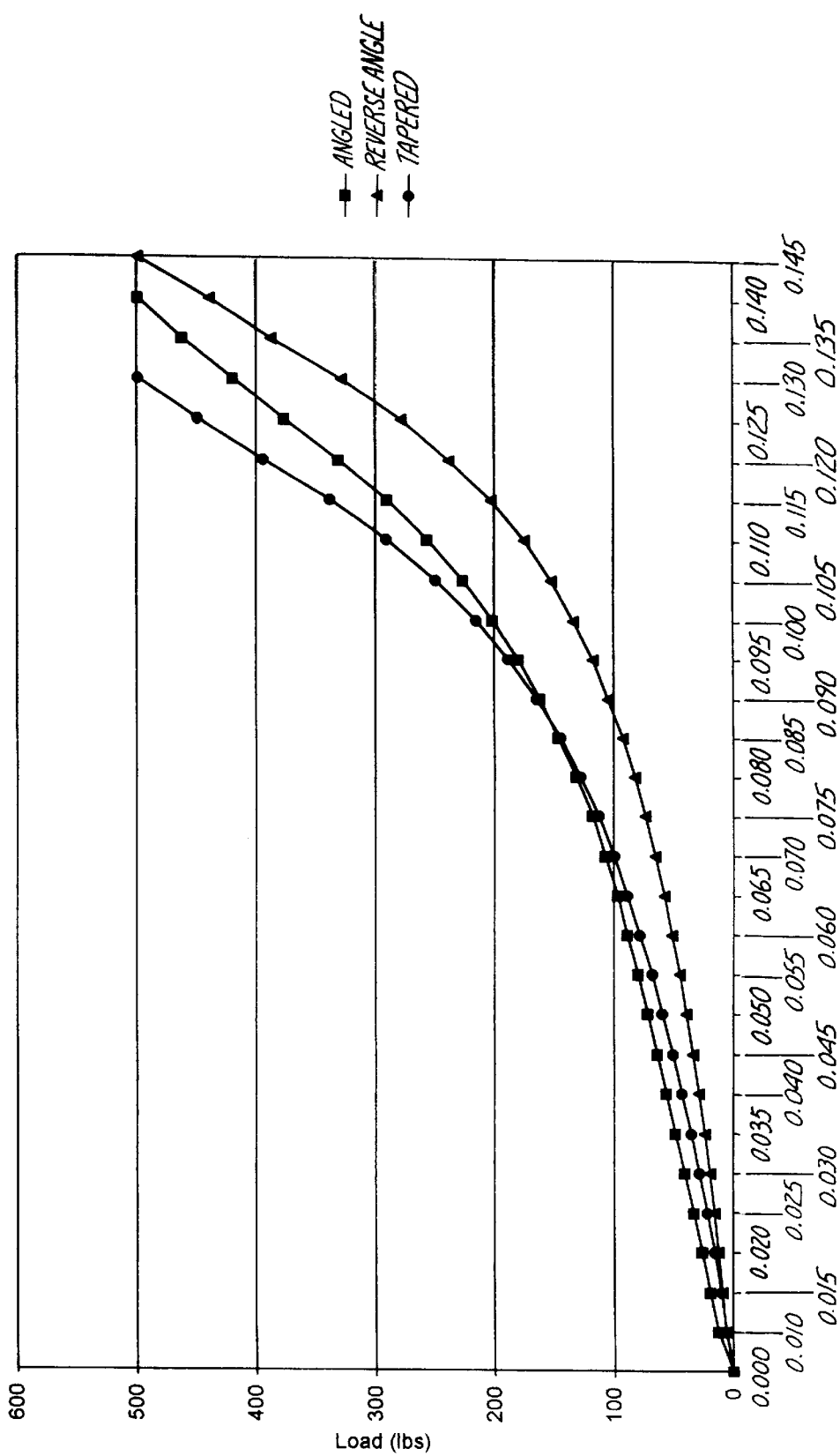

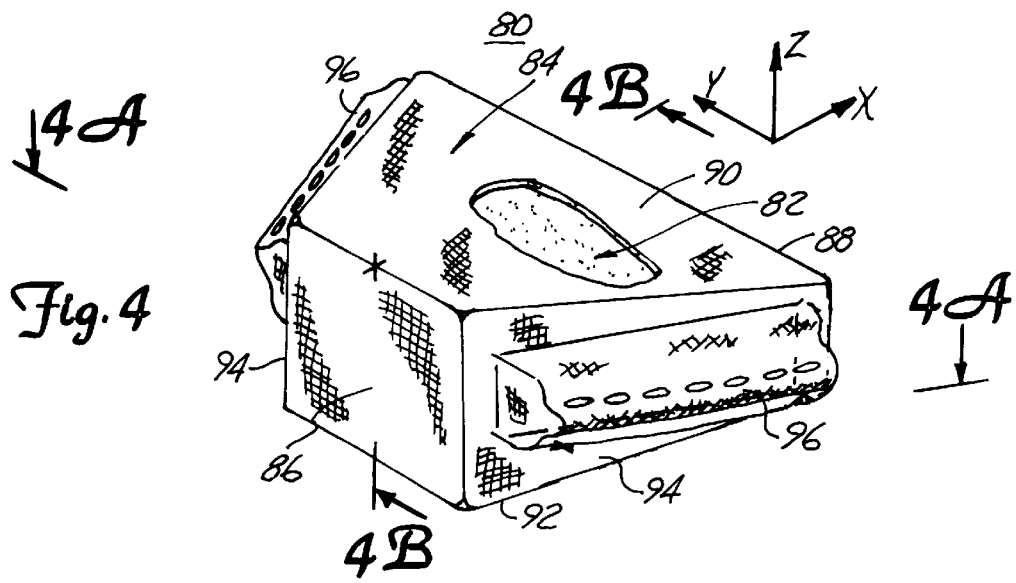
Fig. 4
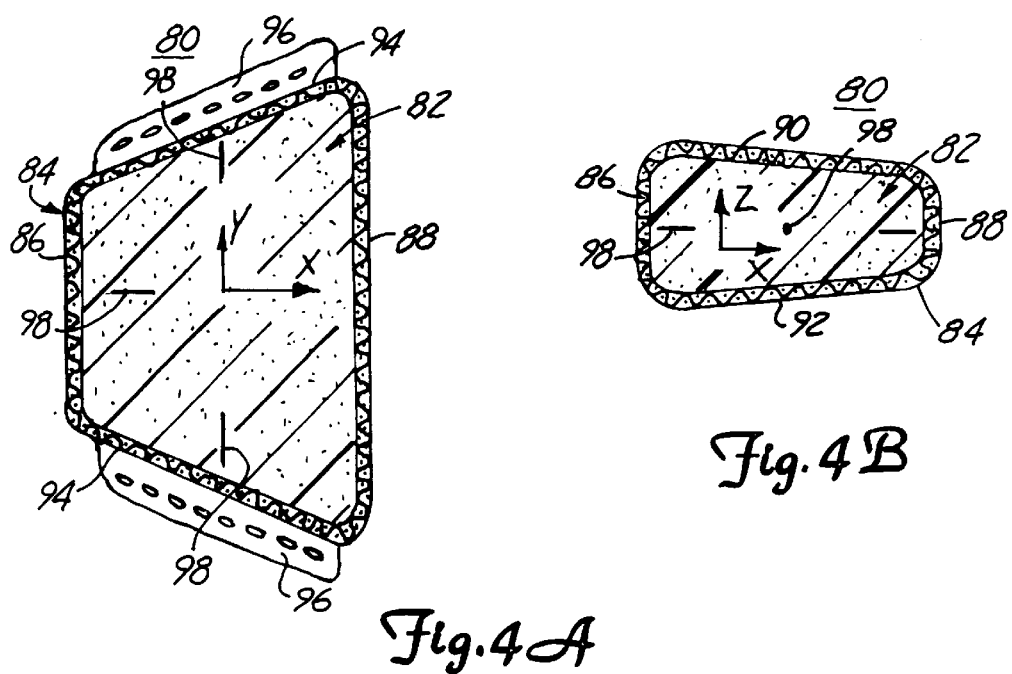
Fig. 4A
Fig. 4B

TAPERED PROSTHETIC SPINAL DISC NUCLEUS

BACKGROUND OF THE INVENTION

The present invention relates to a prosthetic spinal disc nucleus. More particularly, it relates to a prosthetic spinal disc nucleus shaped to correspond generally with the anatomical configuration of an intradiscal space.

The vertebral spine is the axis of the skeleton upon which all of the body parts "hang". In humans, the normal spine has seven cervical, twelve thoracic and five lumbar segments. The lumbar segments sit upon a sacrum, which then attaches to a pelvis, in turn supported by hip and leg bones. The bony vertebral bodies of the spine are separated by intervertebral discs, which act as joints, but allow known degrees of flexion, extension, lateral bending and axial rotation.

The typical vertebra has a thick interior bone mass called the vertebral body, with a neural (vertebral) arch that arises from a posterior surface of the vertebral body. Each narrow arch combines with the posterior surface of the vertebral body and encloses a vertebral foramen. The vertebral foramina of adjacent vertebrae are aligned to form a vertebral canal, through which the spinal sac, cord and nerve rootlets pass. The portion of the neural arch that extends posteriorly and acts to protect a posterior side of the spinal cord is known as the lamina. Projecting from the posterior region of the neural arch is a spinous process. The central portion of adjacent vertebrae is supported by the intervertebral disc.

The intervertebral disc primarily serves as a mechanical cushion between the vertebral bones, permitting controlled motions within vertebral segments of the axial skeleton. The normal disc is a unique, mixed structure, comprised of three component tissues: The nucleus pulposus ("nucleus"), the anulus fibrosus ("anulus"), and two opposing vertebral end plates. The two vertebral end plates are each composed of thin cartilage overlying a thin layer of hard, cortical bone which attaches to the spongy, richly vascular, cancellous bone of the vertebral body. The end plates thus serve to attach adjacent vertebrae to the disc. In other words, a transitional zone is created by the end plates between the malleable disc and the bony vertebrae.

The anulus of the disc is a tough, outer fibrous ring that binds together adjacent vertebrae. This fibrous portion, which is much like a laminated automobile tire, is generally about 10 to 15 millimeters in height and about 15 to 20 millimeters in thickness. The fibers of the anulus consist of 15 to 20 overlapping multiple plies, and are inserted into the superior and inferior vertebral bodies at roughly a 30 degree angle in both directions. This configuration particularly resists torsion, as about half of the angulated fibers will tighten when the vertebrae rotate in either direction, relative to each other. The laminated plies are less firmly attached to each other.

Immersed within the anulus, positioned much like the liquid core of a golf ball, is the nucleus. The anulus and opposing end plates maintain a relative position of the nucleus in what can be defined as a nucleus cavity. The healthy nucleus is largely a gel-like substance having a high water content, and similar to air in a tire, serves to keep the anulus tight yet flexible. The nucleus-gel moves slightly within the anulus when force is exerted on the adjacent vertebrae with bending, lifting, etc.

The nucleus and the inner portion of the anulus have no direct blood supply. In fact, the principal nutritional source for the central disc arises from circulation within the opposing vertebral bodies. Microscopic, villous-like fingerlings of the nuclear and anular tissue penetrate the vertebral end plates and allow fluids to pass from the blood across the cell membrane of the fingerlings and then inward to the nuclear tissue. These fluids are primarily body water and the smallest molecular weight nutrients and electrolytes.

The natural physiology of the nucleus promotes these fluids being brought into, and released from, the nucleus by cyclic loading. When fluid is forced out of the nucleus, it passes again through the end plates and then back into the richly vascular vertebral bodies. The cyclic loading amounts to daily variations in applied pressure on the vertebral column (e.g., body weight and muscle pull) causing the nucleus to expel fluids, followed by periods of relaxation and rest, resulting in fluid absorption or swelling by the nucleus. Thus, the nucleus changes volume under loaded and non-loaded conditions. Further, the resulting tightening and loosening effect on the anulus stimulates the normal anulus collagen fibers to remain healthy or to regenerate when torn, a process found in all normal ligaments related to body joints. Notably, the ability of the nucleus to release and imbibe fluids allows the spine to alter its height and flexibility through periods of loading or relaxation. Normal loading cycling is thus an effective nucleus and inner anulus tissue fluid pump, not only bringing in fresh nutrients, but perhaps more importantly, removing the accumulated, potentially autotoxic by-products of metabolism.

The spinal disc may be displaced or damaged due to trauma or a disease process. A disc herniation occurs when the anulus fibers are weakened or torn and the inner tissue of the nucleus becomes permanently bulged, distended, or extruded out of its normal, internal anular confines. The mass of a herniated or "slipped" nucleus can compress a spinal nerve, resulting in leg pain, loss of muscle control, or even paralysis. Alternatively, with discal degeneration, the nucleus loses its water binding ability and deflates, as though the air had been let out of a tire. Subsequently, the height of the nucleus decreases, causing the anulus to buckle in areas where the laminated plies are loosely bonded. As these overlapping laminated plies of the anulus begin to buckle and separate, either circumferential or radial anular tears may occur, which may contribute to persistent and disabling back pain. Adjacent, ancillary spinal facet joints will also be forced into an overriding position, which may create additional back pain.

Whenever the nucleus tissue is herniated or removed by surgery, the disc space will narrow and may lose much of its normal stability. In many cases, to alleviate pain from degenerated or herniated discs, the nucleus is removed and the two adjacent vertebrae surgically fused together. While this treatment alleviates the pain, all discal motion is lost in the fused segment. Ultimately, this procedure places greater stress on the discs adjacent the fused segment as they compensate for the lack of motion, perhaps leading to premature degeneration of those adjacent discs. A more desirable solution entails replacing in part or as a whole the damaged nucleus with a suitable prosthesis having the ability to complement the normal height and motion of the disc while stimulating the natural disc physiology.

As an alternative to vertebral fusion, various prosthetic discs have been developed. The first prostheses embodied a wide variety of ideas, such as ball bearings, springs, metal spikes and other perceived aids. These prosthetic discs were designed to replace the entire intervertebral disc space and were large and rigid. Beyond the questionable efficacy of these devices were the inherent difficulties encountered during implantation. Due to their size and inflexibility, these devices required an anterior implantation approach as the barriers presented by the lamina and, more importantly, the spinal cord and nerve rootlets during posterior implantation could not be avoided. Recently, smaller and more flexible prosthetic nucleus devices have been developed. With the reduction in prosthesis size, the ability to work around the spinal cord and nerve rootlets during posterior implantation has become possible.

Generally speaking, these reduced sized prostheses are intended to serve as a replacement for the natural nucleus. In other words, the anulus and end plates remain intact, and the prosthesis implanted within the nucleus cavity. It is generally believed that this approach facilitates healing of the anulus. Unfortunately, however, inherent design characteristics of these prostheses may in fact damage the anulus. For example, Bao et al., U.S. Pat. No. 5,047,055, discloses a prosthetic nucleus made of a hydrogel material that is implanted into the intradiscal space in a dehydrated state. Following implant, the hydrogel material hydrates and expands without constraint to, at least in theory, a shape conforming to the natural nucleus. Similarly, Bao et al., U.S. Pat. No. 5,192,326, describes a prosthetic nucleus comprised of a solid hydrogel core or of a multiplicity of hydrogel beads surrounded by a membrane. Once again, this prosthesis is implanted into the disc space in a dehydrated state, subsequently hydrating, at least in theory, to a shape conforming to the natural nucleus. The prostheses of Bao, as well as other similar products, rely solely upon the natural anulus to constrain expansion of the hydrogel core. Obviously, this essentially uncontrolled expansion imparts a lateral force directly upon the anulus. In most situations, the anulus is already damaged, and any additional forces placed on the anulus by the prosthesis may impede healing and even cause further deterioration. Further, it is virtually impossible to accurately orientate the dehydrated prostheses of Bao within the nucleus cavity due to the confined environment.

In addition to the above-described concern for minimizing stress on the anulus, anatomical variations of the nucleus cavity should also be considered. Generally speaking, each intradiscal space has a greater transverse diameter (as defined by opposing end plates) at a posterior side than at an anterior side. Additionally, the intradiscal space varies in height (as defined by the opposing end plates) from posterior side to anterior side. In this regard, each intradiscal space has a relatively unique height configuration. For example, the L3-L4 intradiscal space has a slightly greater height at a central area in comparison to the posterior and anterior sides. The L4-L5 intradiscal space displays a more dramatic increase in height at the central area. Finally, the L5-S1 intradiscal space increases in height from the posterior side to the anterior side. Effectively, each intradiscal space can be generally referred to as having an anterior area or compartment and a posterior area or compartment, although it should be understood that there is no wall, membrane, etc. residing in the intradiscal space to otherwise specifically delineate separate "compartments." With these dimensional variations in mind, a "standard" or single-sized prosthesis likely will not meet the anatomical needs of each and every intradiscal space. This is especially true for a single, rigid prosthesis design sized to encompass the entire intradiscal space and that therefore does not recognize the general distinction between the anterior area or compartment and the posterior area or compartment. Additionally, a prosthetic nucleus that fails to account for the anatomical variation in height of the nucleus cavity may result in an uneven load distribution across the prosthesis and therefore poor spacing performance.

Finally, restoring the nutrition-flushing cycle of a natural disc is important for a prosthetic spinal disc nucleus to be successful. As previously described, most of the nutrition for the inner anulus and nucleus is provided by diffusion through the end plates of the vertebral bodies and by the important pumping action between the partially loaded and fully loaded conditions of the disc. If the nutritional cycle is impeded, a variety of degenerative changes may occur. Nutrition to the inner disc slowly ceases, resulting in intradiscal build-up of acids and autotoxins, and other changes. This is followed by nuclear and anular fiber degeneration, shrinkage of the nucleus, segmental laxity, spur formation, disc space collapse and perhaps spontaneous fusion. Additionally, significantly disabling back pain may develop. Thus, a prosthetic nucleus sized to encompass the entire nucleus cavity prevents the fluid pumping action of the disc space from occurring, and will not result in complete healing.

Degenerated, painfully disabling intraspinal discs are a major economic and social problem for patients, their families, employers and the public at large. Any significant means to correct these conditions without further destruction or fusion of the disc may therefore serve an important role. Other means to replace the function of a degenerated disc have major problems such as complex surgical procedures, unproven efficacy, placing unnecessary and possibly destructive forces on an already damaged anulus, etc. Therefore, a substantial need exists for a prosthetic spinal disc nucleus, formed to address anatomical variations, that restores the size, load-bearing ability and pumping action of a normal disc while minimizing trauma to the disc space.

SUMMARY OF THE INVENTION

The present invention provides an elongated prosthetic spinal disc nucleus for implantation deep inside a nucleus cavity, defined by opposing end plates and an anulus, and a method of manufacturing such a prosthesis. In a preferred embodiment, the prosthesis is comprised of a hydrogel core surrounded by a constraining jacket.

The hydrogel core is configured to expand from a dehydrated state to a hydrated state and is formed to a wedge-shape in at least the hydrated state. In one preferred embodiment, the hydrogel core defines an anterior face and a posterior face corresponding to a transverse plane of the nucleus cavity. The hydrogel core is formed such that in the hydrated state, the hydrogel core tapers between the anterior face and the posterior face.

The constraining jacket surrounds the hydrogel core and constrains expansion upon hydration. The constraining jacket is preferably flexible but substantially inelastic, having a generally fixed maximum volume less than a volume of the nucleus cavity. In one preferred embodiment, the volume of the constraining jacket is greater than the volume of the hydrogel core in the unhydrated state, but less than a theoretical, unconstrained volume of the hydrogel core in the hydrated state. Thus, the constraining jacket is configured to prevent the hydrogel core from conforming to the anulus upon hydration.

The preferred method of manufacturing a prosthetic spinal disc nucleus in accordance with the present invention includes forming a core of hydrogel material to an approximately wedge shape. The hydrogel core, in a dehydrated state, is then inserted into a substantially inelastic constraining jacket. In one preferred embodiment, the assembled prosthetic spinal disc nucleus is conditioned to ensure a known load-bearing ability.

The prosthetic spinal disc nucleus is implanted into the nucleus cavity with the hydrogel core in a dehydrated state. Once inserted, the prosthetic spinal disc nucleus is orientated to extend transversely, corresponding generally with the shape of the nucleus cavity. In one preferred embodiment, the prosthetic spinal disc nucleus is orientated within the nucleus cavity such that an anterior face of the prosthesis is adjacent an anterior side of the anulus, whereas a posterior face is centrally located within the nucleus cavity. In another preferred embodiment, the posterior face of the prosthetic is positioned adjacent a posterior side of the anulus, whereas the anterior face resides in a central area of the nucleus cavity. Regardless of the exact positioning, the prosthetic spinal disc nucleus of the present invention corresponds generally to the anatomical spacing of the disc space. For example, where the posterior face of the prosthetic spinal disc nucleus is positioned adjacent a posterior side of a L4-L5 disc space, the hydrogel core is tapered to increase in height from the posterior face to the anterior face, in conformance with naturally occurring variations in the L4-L5 disc space. In one preferred embodiment, two prosthetic spinal disc nuclei are positioned side-by-side in the nucleus cavity, each corresponding generally to the anatomical shape of the respective side (or general area or compartment) of the nucleus cavity.

Following implant, the hydrogel core begins to hydrate and expand. Once the hydrogel core has expanded to a horizontal limit of the constraining jacket, the constraining jacket directs further expansion so that the prosthetic spinal disc nucleus increases substantially in height. Throughout the hydration process, the hydrogel core expands proportionally, generally maintaining its pre-formed shape.

The prosthetic spinal disc nucleus of the present invention reestablishes near-normal disc height and near-normal anulus position and function. In this regard, the anatomical-related shape of the prosthetic spinal disc nucleus promotes an increase in surface area contact between the prosthetic spinal disc nucleus and opposing end plates, and a relatively even stress distribution. Following implantation, the prosthetic spinal disc nucleus works in concert with the remaining disc components to restore the natural physiology of a human disc. In response to the removal and exertion of compressive loads on the disc space, the restored disc will imbibe and expel fluids during the natural cyclic pumping of the discal area.

BRIEF DESCRIPTION OF THE DRAWINGS

FIG. 2 is a graph showing a compression modulus of elasticity of the prosthetic spinal disc nucleus of the present invention following conditioning;

FIG. 4 is a perspective view of an alternative embodiment of a prosthetic spinal disc nucleus in a hydrated state, including a cutaway view showing a portion of a hydrogel core, in accordance with the present invention;

FIG. 4A is a top, sectional view of the prosthetic spinal disc nucleus of FIG. 4 along the line A—A;

FIG. 4B is a side, sectional view of the prosthetic spinal disc nucleus of FIG. 4 along the line B—B;

DETAILED DESCRIPTION OF THE PREFERRED EMBODIMENTS

A. Prosthetic Spinal Disc Nucleus 20

Figure 1:
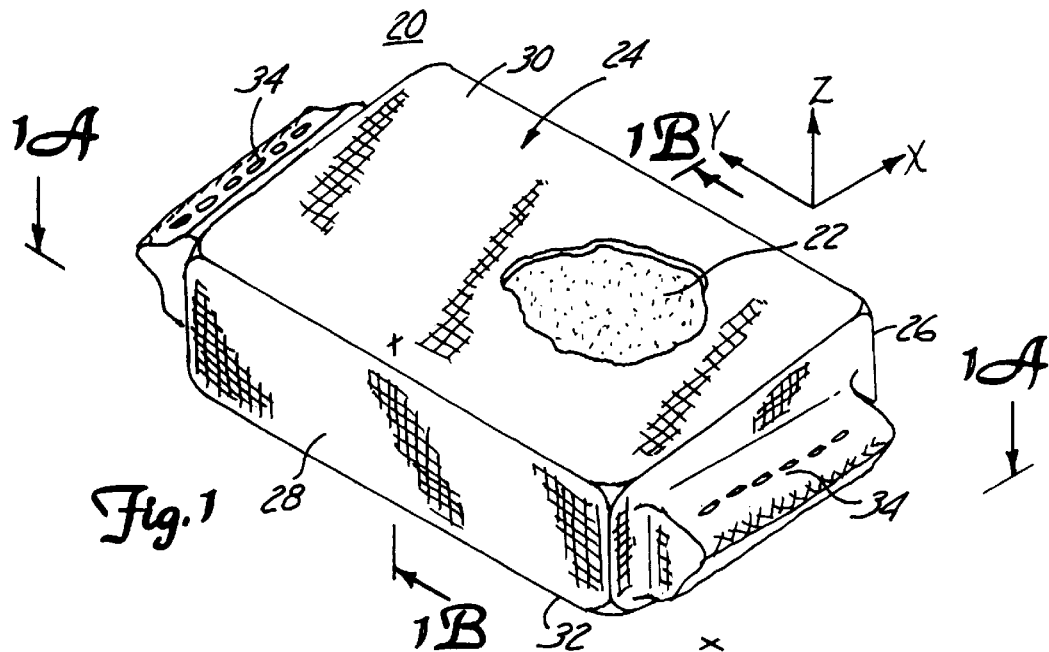
FIG. 1 is a perspective view of a prosthetic spinal disc nucleus in a hydrated state, including a cutaway view showing a portion of a hydrogel core, in accordance with the present invention.

One preferred embodiment of a prosthetic spinal disc nucleus 20 is shown in FIG. 1. The prosthetic spinal disc nucleus 20 is comprised of a hydrogel core 22 and a constraining jacket 24. The prosthetic spinal disc nucleus 20 defines an anterior face 26 (shown partially in FIG. 1), a posterior face 28, a superior face 30 and an inferior face 32 (shown partially in FIG. 1). The constraining jacket 24 is secured around the hydrogel core 22 by closures 34 located at opposite ends of the constraining jacket 24. For the purposes of this disclosure, directional terminology such as "anterior," "posterior," "superior," and "inferior" are with reference to one possible orientation of the prosthetic spinal disc nucleus 20 within a nucleus cavity (not shown). It should be understood, however, that due to its unique sizing, the prosthetic spinal disc nucleus 20 can be orientated in any direction relative to a nucleus cavity or the world in general. As such, the directional terms are provided for purposes of illustration only, and should not be interpreted as limitations.

Figure 1A:
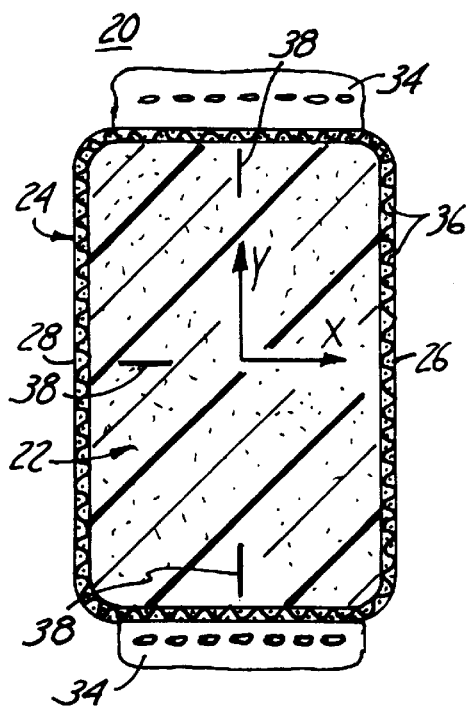
FIG. 1A is a top, sectional view of the prosthetic spinal disc nucleus of FIG. 1 along the line A—A.
Figure 1B:
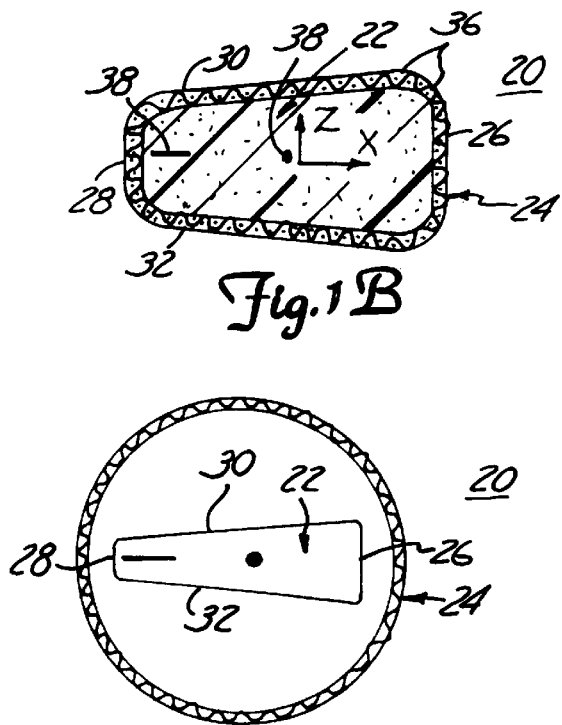
FIG. 1B is a side, sectional view of the prosthetic spinal disc nucleus of FIG. 1 along the line B—B.

As shown more clearly in FIGS. 1A and 1B, the hydrogel core 22, and thus the prosthetic spinal disc nucleus 20, is fabricated to assume an elongated wedge shape. In this regard, a top, cross-sectional view of the prosthetic spinal disc nucleus 20 (FIG. 1A) shows the hydrogel core 22 as being substantially rectangular. Additionally, a side, cross-sectional view (FIG. 1B) depicts the hydrogel core 22 as tapered or wedge shaped. With reference to FIG. 1A, the top sectional view of the prosthetic spinal disc nucleus 20 defines a width ("x" in FIG. 1A) and a length ("y" in FIG. 1A). Further, the side sectional view of the prosthetic spinal disc nucleus 20 defines the width ("x" in FIG. 1B) and a height ("z" in FIG. 1B). As shown in FIG. 1B, the hydrogel core 22, and thus the prosthetic spinal disc nucleus 20, has a height ("z") increasing from the posterior face 28 to the anterior face 26.

In a preferred embodiment, the hydrogel core 22 is configured to imbibe fluids, expanding from a dehydrated state to a hydrated state. In this regard, the hydrogel core 22 is preferably formulated as a mixture of hydrogel polyacrylonitrile. In particular, acrylamide and acrylonitrile (block co-polymer) are used. Alternatively, the hydrogel core 22 can be any hydrophilic acrylate derivitive with a unique multiblock co-polymer structure or any other hydrogel material having the ability to deform and reform in a desired fashion in response to placement and removal of loads. Even further, a biologically safe polymer that can imbibe fluids while maintaining its structure under various stresses is acceptable. For example, the hydrogel core 22 can be formulated as a mixture of polyvinyl alcohol and water. Much like a normal human nucleus, the hydrogel core 22 will initially swell from a dehydrated state as it absorbs fluid. When hydrated, the hydrogel core 22 will have a water content of 25–90 percent. The hydrogel material 22 of the preferred embodiment is manufactured under the trade name HYPAN® by Hymedix International, Inc. of Dayton, N.J.

Completely surrounding the hydrogel core 22 is the constraining jacket 24. The constraining jacket 24 is preferably a flexible tube made of tightly woven high molecular weight, high tenacity polymeric fabric. In a preferred embodiment, high molecular weight polyethylene is used as the weave material of the constraining jacket 24. However, polyesther or any high molecular weight, high tenacity polymeric material can be employed, and carbon fiber yarns, ceramic fibers, metallic fibers, etc., also are acceptable.

The constraining jacket 24 is preferably made of fibers that have been highly orientated along their length. As a result, the constraining jacket 24 material, while flexible, has little elasticity or stretch. Thus, the constraining jacket 24 defines a horizontal limit (in the x-y plane of FIG. 1A) and a generally fixed maximum volume. In one preferred embodiment, the generally fixed maximum volume of the constraining jacket 24 is less than a theoretical volume of the hydrogel core 22 if allowed to completely hydrate without constraint. Thus, because the hydrogel core 22 has a natural volume greater than the constraining jacket 24, the constraining jacket 24 will be tight about the hydrogel core 22 when hydrated, as described in greater detail below. Finally, the volume differential between the constraining jacket 24 and the hydrated hydrogel core 22 serves to extend the useful life of the prosthetic spinal disc nucleus 20. In particular, the constraining jacket 24 effectively prevents the hydrogel core 22 from reaching its natural hydration level. Consequently, the hydrogel 22 will have a constant affinity for imbibing additional fluid.

The preferred woven construction of the constraining jacket 24 creates a plurality of small openings 36. Each of the plurality of the small openings 36 is large enough to allow bodily fluids to interact with the hydrogel core 22 otherwise maintained within the constraining jacket 24. However, each of the plurality of small openings 36 is small enough to prevent the hydrogel core 22 from escaping. Preferably, each of the plurality of small openings 36 has an average diameter of about 10 micrometers, although other dimensions are acceptable. In this regard, while the constraining jacket 24 has been described as having a weave configuration, any other configuration having a semipermeable or porous attribute can be used. Finally, the constraining jacket 24 material preferably allows for tissue in-growth and is textured to provide a grip or purchase within a disc space (not shown).

The prosthetic spinal disc nucleus 20 is manufactured substantially as follows. First, the hydrogel core 22 is formulated. An appropriate volume of hydrogel material, suspended in a solvent, is poured into a mold having the preferred wedge shape. Once cast, a solvent exchange process is performed, replacing the solvent with water such that the hydrogel material hydrates to a maximum hydration level.

In the hydrated state, the hydrogel core 22 is relatively soft. To aid in ensuring proper placement of the prosthetic spinal disc nucleus 20 within an intervertebral disc space and to review the stability of the prosthetic spinal disc nucleus 20 during patient follow-ups, three radiopaque wires 38 are preferably forced into the hydrogel core 22. The radiopaque wires 38 are located within the hydrogel core 22 to define the overall shape, as shown in FIG. 1A. As described below, the radiopaque wires 38 further provide an indication of a location of the prosthetic spinal disc nucleus 20 upon implant. The radiopaque wires 38 are preferably made of a platinum-iridium material, but can be any other material having radiopaque and biologically inert characteristics. Notably, the preferred platinum-iridium material is visible by normal, inexpensive x-ray procedures, as well as by computer generated imaging. In a preferred embodiment, the radiopaque wires 38 are each approximately 2 millimeters in length, although other dimensions are useful.

The hydrogel core 22 is then preferably placed in an oven and dehydrated, resulting in an under-sized, wedge shaped body. The hydrogel core 22, in a dehydrated state, is inserted into the constraining jacket 24.

Prior to insertion of the hydrogel core 22, the constraining jacket 24 is an elongated, open ended tube, and does not include the closures 34. The dehydrated hydrogel core 22 is inserted axially into the constraining jacket 24 through one of the open ends and centrally positioned. The open ends of the constraining jacket 24 are then secured by forming the closures 34. For example, the material at the open ends may be folded and then closed by sewing a dense, bar-tack stitch at a position near the hydrogel core 22. The bar-tack stitch material is preferably the same high tenacity, high polymeric material, such as a high molecular weight polyethylene, as is used for the constraining jacket 24. By employing the same material for both the constraining jacket 24 and the bar-tack stitch, the biocompatability of the entire prosthetic spinal disc nucleus 20 is ensured. Any excess material is removed from the constraining jacket 24 by a thermal cut. This thermal cut fuses the potentially fraying ends of the constraining jacket 24 distal the stitching.

Following closure of the constraining jacket 24 about the hydrogel core 22, the prosthetic spinal disc nucleus 20 is rehydrated. In particular, the hydrogel core 22 is allowed to hydrate and expand to a volumetric limit of the constraining jacket 24. The integrity of the constraining jacket 24 in this expanded state is then reviewed, confirming stability of the closures 34. If the closures 34, or any other portion of the constraining jacket 24, fail, the prosthetic spinal disc nucleus 20 is either discarded or the hydrogel core 22 inserted into a new constraining jacket.

Assuming the constraining jacket 24 and the closures 34 do not fail, the hydrogel core 22 is then dehydrated and "conditioned". This conditioning amounts to at least three compressive loads being applied across the length (or opposing end plate faces 30, 32) of the prosthetic spinal disc nucleus 20. The selected magnitude of the compressive loads relates to in vivo compressive loads normally encountered by a patient. In this regard, the magnitude of in vivo compressive loads varies from patient to patient and is a function of the patient's size and spinal level. For example, published literature has stated that the normal standing or sitting compressive load on the discal area is 1.8 multiplied by the patient's body weight. Further, the maximum compressive load placed on the lumbar discal area during normal, daily activities is 3.6 multiplied by the patient's body weight. The conditioning, therefore, will consist of a series of compressive loads being placed upon the prosthetic spinal disc nucleus 20 equivalent to a minimum of 1.8 multiplied by a typical body weight, up to a maximum of 3.6 multiplied by a typical body weight.

With reference to FIG. 1B, the compressive loads are applied along a plane substantially normal to the opposing superior and inferior faces 30, 32. To accomplish this effect, the hydrogel core 22 is preferably maintained within a tapered clamp configured to maintain the wedge shape of the hydrogel core 22. The compressive loads act to flatten the prosthetic spinal disc nucleus 20 such that there is a significant decrease in height (z-axis in FIG. 1B), and a slight increase in length (y-axis in FIG. 1A) and width (x-axis in FIGS. 1A and 1B).

As a result of the above-described conditioning, in combination with other elements such as size, shape, etc., the hydrogel core 22, and thus the prosthetic spinal disc nucleus 20, will have a known load bearing ability. The resulting hydrogel core 22 is viscoelastic, having a defined cross-sectional area and thickness, as well as a defined compression modulus of elasticity, as shown, for example, in FIG. 2. The graph provided in FIG. 2 represents the change in height of the prosthetic spinal disc nucleus 20 (and two other alternative embodiments of the prosthetic spinal disc nucleus 20 described elsewhere) in response to various loads. Due to conditioning, the hydrogel core 22, and thus the prosthetic spinal disc nucleus 20, will consistently adhere to the curve shown in FIG. 2. The conditioning ensures that the hydrogel core 22 is deformable, but essentially is not compressible.

Returning to FIG. 1, as a further benefit, the manufacturing process places a volume expansion constraint on the hydrogel core 22. Even if the hydrogel core 22 were unconstrained (e.g., if the constraining jacket 24 ruptures), following conditioning the hydrogel core 22 will not expand to more than twice its initial volume. Thus, a continuous, unlimited, potentially hazardous swelling of the hydrogel core 22 will not occur should the constraining jacket 24 be disrupted. This internalized constraint will also prevent possible over-expansion of the hydrogel core 22 if the prosthetic spinal disc nucleus 20 is continually unloaded in the disc space or if the prosthetic spinal disc nucleus 20 were to be displaced into another body cavity, such as the spinal canal or abdomen.

Figure 1C:
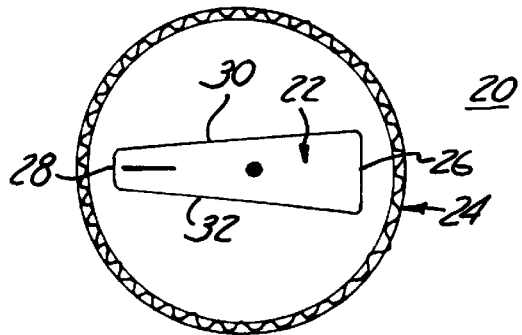
FIG. 1C is the side, sectional view of FIG. 1B with the hydrogel core in a dehydrated state.

Following conditioning, the prosthetic spinal disc nucleus 20 is dehydrated, preferably by retaining the prosthetic spinal disc nucleus 20 in a wedge-shaped clamp and then placing the entire assembly in an oven. In the dehydrated state, the constraining jacket 24 is loose about the hydrogel core 22, as shown in FIG. 1C. Notably, for purposes of illustration, FIG. 1C exaggerates the difference in size between the hydrogel core 22 and the constraining jacket 24. Further, while the constraining jacket 24 is depicted as being circular in cross-section, it should be recalled the constraining jacket 24 is preferably flexible such that with the hydrogel core 22 in the dehydrated state, the constraining jacket 24 can be collapsed to a wide variety of shapes. It should also be noted that during the final dehydration step, the hydrogel core 22 can be forced to a shape different than that shown in FIG. 1C. For example, it may be desirable for the hydrogel core 22 to be entirely flat. Regardless of the final, dehydrated shape, upon hydration, the hydrogel core 22 will expand to the shape shown in FIGS. 1A and 1B due to the shape memory attribute of the hydrogel material.

Prior to implant, the prosthetic spinal disc nucleus 20 is preferably maintained, in a dehydrated state, within a retaining tube (not shown) size to maintain the generally wedge shape of the hydrogel core 22. The retaining tube is preferably made of implantable grade stainless steel, but can be any other surgically safe material such as polyethylene. The prosthetic spinal disc nucleus 20 and its retaining tube may be packaged in a dry foam. The entire surgical package is sterilized in a tray, via gamma, steam or other form of sterilization. Once conditioned, retained, and sterilized, the dehydrated prosthetic spinal disc nucleus 20 is ready for implantation into the human disc space.

As described in greater detail below, following implantation, the hydrogel core 22 hydrates and expands, the expansion being constrained by the constraining jacket 24. In a final hydrated form, the prosthetic spinal disc nucleus 20 will have an overall length in the range of approximately 10–38 millimeters, a width in the range of approximately 10–15 millimeters, and a maximum height in the range of approximately 3–17 millimeters. Because, as described below, the closures 34 do not contact or otherwise support opposing vertebrae, the effective working length of the prosthetic spinal disc nucleus 20 is the length (y-axis in FIG. 1A) of the hydrogel core 22, as constrained by the constraining jacket 24 in a hydrated state. In a preferred embodiment, the working length of the prosthetic spinal disc nucleus 20 is in the range of approximately 9–24 millimeters. With respect to the maximum height range provided, it should be recalled that the prosthetic spinal disc nucleus 20 preferably forms a wedge shape, tapering in height. With reference to FIG. 1B, each of the superior face 30 and the inferior face 32 form an included angle in the range of approximately 2–10 degrees. For example, the superior face 30 forms an angle with the posterior face 28 in the range of approximately 91–95 degrees; and an angle with the anterior face 26 in the range of approximately 85–89 degrees. It should be recognized, however, that the hydrogel core 22 can be configured to taper at an even greater angle of inclination. The height of the anterior face 26 (or maximum working height of the prosthetic spinal disc nucleus 20) is approximately 3–17 millimeters. The height of the posterior face 26 (or minimum working height of the prosthetic spinal disc nucleus 20) is approximately 2–15 millimeters.

The preferred prosthetic spinal disc nucleus 20 in final hydrated form, for a medium sized disc space, is 20 millimeters in overall length, 13.5 millimeters in width, 10 millimeters in maximum working height (or anterior face height) and 8.5 millimeters in minimum height. These dimensions conform to the approximate length of the transverse diameter, one-half the approximate sagittal diameter and the approximate height of an adult human disc space, which normally varies in height along its length. In this regard, the hydrogel core 22 preferably tapers in height to an included angle of 6 degrees to form the preferred wedge shape. Importantly, the height (z-axis in FIG. 1B) of the prosthetic spinal disc nucleus 20 will be greatly reduced when the hydrogel core 22 is in a dehydrated state.

It is realized that not all non-human discs are of the same size. Therefore, the prosthetic spinal disc nucleus 20, in final hydrated form, alternatively is constructed to assume dimensions of 20 millimeters in length, posterior face height of 7 millimeters and anterior face height of 8 millimeters; length of 20 millimeters, anterior face height of 12 millimeters and posterior face height of 10 millimeters; length of 25 millimeters, anterior face height of 8 millimeters and posterior face height of 7 millimeters; length of 25 millimeters, anterior face height of 10 millimeters and posterior face height of 8.5 millimeters; and length of 25 millimeters, anterior face height of 12 millimeters and posterior face height of 10 millimeters. The appropriate prosthetic nucleus for a particular patient is determined by various diagnostic procedures prior to and during surgery. Basically, the properly dimensioned prosthesis is a function of a patient's size and spinal level. By making available varying dimensions for the prosthetic spinal disc nucleus 20, the space requirements reflected by any spinal segment, human or animal, are satisfied.

B. Prosthetic Spinal Disc Nucleus 50

Figure 3:
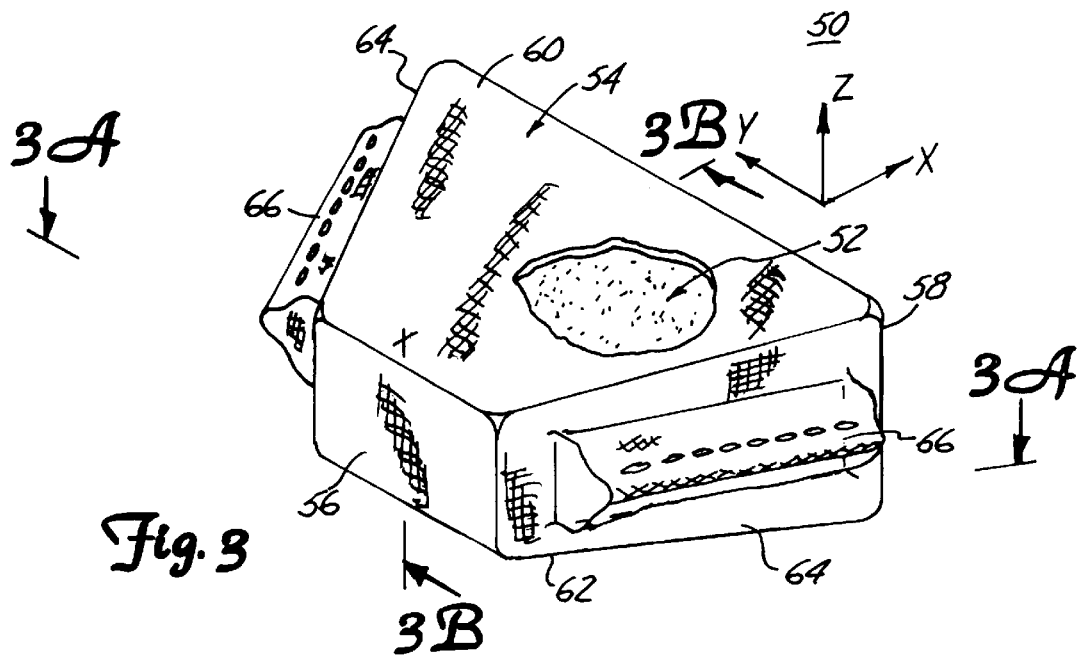
FIG. 3 is a perspective view of an alternative embodiment of a prosthetic spinal disc nucleus in a hydrated state, including a cutaway view showing a portion of a hydrogel core, in accordance with the present invention.

As will be described in greater detail below, one advantage of a prosthesis of the present invention is general conformance to the anatomical shape of a general area or compartment of a disc space. For example, the prosthetic spinal disc nucleus 20 has been shown as generally assuming a wedge shape, tapering in height. It should be understood, however, that an individual disc space or intradiscal area/compartment may present additional anatomical variations. In recognition of these anatomical variances, the prosthetic spinal disc nucleus 20 in accordance with the present invention may assume other shapes. For example, an alternative embodiment of a prosthetic spinal disc nucleus 50 is shown in FIG. 3. The prosthetic spinal disc nucleus 50 is highly similar to the prosthetic spinal disc nucleus 20 previously described and is comprised of a hydrogel core 52 surrounded by a constraining jacket 54. The prosthetic spinal disc nucleus 50 has an anterior face 56, a posterior face 58 (shown partially in FIG. 3), a superior face 60, an inferior face 62 (shown partially in FIG. 3) and opposing end walls 64. The constraining jacket 54 is secured around the hydrogel core 52 by closures 66.

Figure 3A:
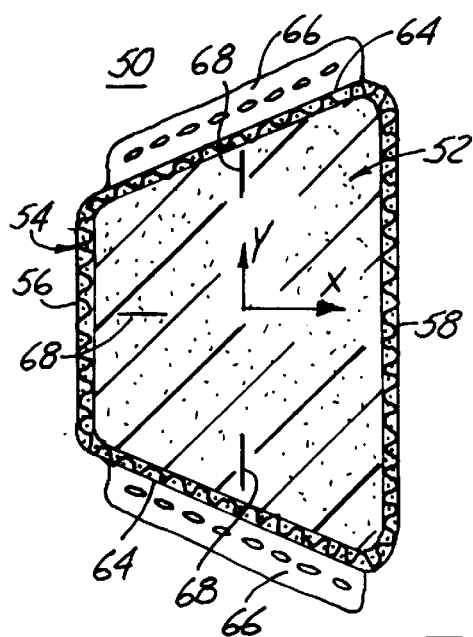
FIG. 3A is a top, sectional view of the prosthetic spinal disc nucleus of FIG. 3 along the line A—A.
Figure 3B:
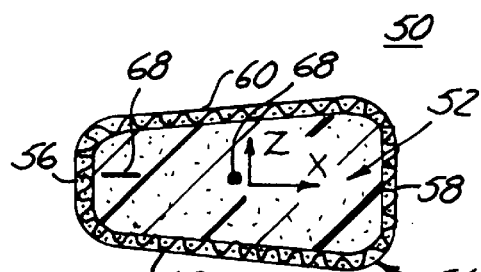
FIG. 3B is a side, sectional view of the prosthetic spinal disc nucleus of FIG. 3 along the line B—B.

As shown in FIGS. 3A and 3B, the prosthetic spinal disc nucleus 50 is fabricated to assume an angled, wedge shape. For this reason, it should be understood that the alternative prosthetic spinal disc nucleus 50 can be referenced as an "angled prosthetic spinal disc nucleus," whereas the prosthetic spinal disc nucleus 20 (FIG. 1) can be referred to as a "tapered prosthetic spinal disc nucleus." FIG. 3A shows the superior and inferior faces 60, 62 as being approximately trapezoidal or wedge-shaped, tapering in length (y-axis) from the posterior face 58 to the anterior face 56. FIG. 3B depicts the tapered or wedge-shape of the prosthetic spinal disc nucleus 50 in which the height (z-axis) decreases from the posterior face 58 to the anterior face 56. The angled prosthetic spinal disc nucleus 50 is highly similar to the previously described tapered prosthetic spinal disc nucleus 20 except for the generally trapezoidal shape of the superior and inferior faces 60, 62 (or decrease in length from the posterior face 58 to the anterior face 56).

The material used for the hydrogel core 52 is identical to that previously described and is formulated as a mixture of hydrogel polyacrylonitrile. In particular, acrylamide and acrylonitrile (block co-polymer) are used. Alternatively, the hydrogel core 52 can be any hydrophilic acrylate derivative with a unique multi-block co-polymer structure or any other hydrogel material having the ability to deform and reform in a desired fashion in response to placement and removal of loads. The hydrogel material of the preferred embodiment is manufactured under the trade name HYPAN® by Hymedix International, Inc. of Dayton, N.J.

The constraining jacket 54 is likewise virtually identical in construction to the constraining jacket 24 (FIG. 1) previously described. Once again, the constraining jacket 54 is flexible but substantially inelastic, defining a horizontal limit (x-y plane of FIG. 3A) and a generally fixed maximum volume.

The angled prosthetic spinal disc nucleus 50 is constructed in a manner highly similar to that previously described, with the hydrogel core 52 being preshaped and dehydrated prior to insertion within the constraining jacket 54. Radiopaque wires 68 are also provided. The closures 66 are formed to support and conform to the angular portion of the superior and inferior faces 60, 62. In other words, each of the closures 66 extend generally parallel to a respective one of the opposing side walls 64, as shown in FIG. 3A. The angled prosthetic spinal disc nucleus 50 is conditioned prior to implant. This conditioning renders the hydrogel core 52 to a flattened shape and results in a known load-bearing ability, shown in FIG. 2.

Returning to FIGS. 3–3B, in one preferred embodiment, the hydrogel core 52 is preferably preshaped to taper in height (z-axis in FIG. 3B) from the posterior face 58 to the anterior face 56, forming an included angle in the range of approximately 2–10 degrees, preferably 6 degrees. For example, the superior face 60 forms an angle with the posterior face 58 in the range of approximately 85–89 degrees; and an angle with the anterior face 56 in the range of approximately 91–95 degrees. The relationship of the inferior face 62 with the posterior face 58 and the anterior face 56 is preferably identical but need not necessarily be symmetrical. Further, with reference to FIG. 3A, the hydrogel core 52 is preshaped to taper in length (y-axis in FIG. 3A) from the posterior face 58 to the anterior face 56, forming an included angle in the range of approximately 50–70 degrees, preferably 60 degrees. For example, as show in FIG. 3A, each of the opposing end walls 64 forms an angle in the range of approximately 115–125 degrees, preferably 120 degrees, with the anterior face 56; and an angle in the range of approximately 55–65 degrees, preferably 60 degrees, with the posterior face 58. It should be recognized that other angles, either greater or smaller, are also acceptable. Additionally, the opposing end walls 64 may be non-symmetrical relative to one another.

With these characteristics of the hydrogel core 52 in mind, the angled prosthetic spinal disc nucleus 50, in a final hydrated form, has an overall length in the range of approximately 23–33 millimeters, a posterior face height (or maximum working height) in the range of approximately 6–14 millimeters, an anterior face height (or minimum working height) in the range of approximately 4–12 millimeters, and a width in the range of approximately 10–14 millimeters. Because, as described below, the closures 64 do not contact or otherwise support opposing vertebrae, the effective working length of the angled prosthetic spinal disc nucleus 50 is the length of the hydrogel core 52 as constrained by the constraining jacket 54 in a hydrated state. With this in mind, the angled prosthetic spinal disc nucleus 50 has a posterior face length (or maximum working length) in the range of approximately 18–22 millimeters, and an anterior face length (or minimum working length) in the range of approximately 11.5–15.5 millimeters.

In one specific example relating to an average sized disc space, the angled prosthetic spinal disc nucleus 50 preferably has, in final hydrated form, an overall length of 28 millimeters, a maximum working (or posterior face) height of 10 millimeters, a minimum working (or anterior face) height of 8.5 millimeters, a width of 12.5 millimeters, a maximum working (or posterior face) length of 20 millimeters and a minimum working (or anterior face) length of 13.5 millimeters. It should be recognized, however, that the above-provided dimensions can vary widely such that the angled prosthetic spinal disc nucleus 50 is properly sized for placement within any individual disc space. Additionally, the height (z-axis in FIG. 3B) of the angled prosthetic spinal disc nucleus 50 will be greatly reduced when the hydrogel core 52 is in the dehydrated state.

C. Prosthetic Spinal Disc Nucleus 80

Yet another alternative embodiment of a prosthetic spinal disc nucleus 80 is shown in FIG. 4. The prosthetic spinal disc nucleus 80 is highly similar to previous embodiments and includes a hydrogel core 82 and a constraining jacket 84. Once again, the prosthetic spinal disc nucleus 80 defines an anterior face 86, a posterior face 88 (shown partially in FIG. 4), a superior face 90, an inferior face 92 (shown partially in FIG. 4), and opposing end walls 94. The constraining jacket 84 is secured around the hydrogel core 82 by closures 96.

The composition and structure of the hydrogel core 82 and the constraining jacket 84 are virtually identical to those previously described. The actual shape, however, of these components differs somewhat. In particular, the prosthetic spinal disc nucleus 80 assumes an angled, wedge-shape. With reference to FIGS. 4A and 4B, this shape has a reverse angular shape when compared to the angled prosthetic spinal disc nucleus 50 (FIG. 3). For this reason, the alternative prosthetic spinal disc nucleus 80 can be referred to as a "reverse angle prosthetic spinal disc nucleus."

The reverse angle prosthetic spinal disc nucleus 80 again tapers in length (y-axis in FIG. 4A) from the posterior face 88 to the anterior face 86 such that the superior and inferior faces 90, 92 are approximately trapezoidal. In particular, with reference to FIG. 4A, the reverse angle prosthetic spinal disc nucleus 80 tapers in length (y-axis in FIG. 4A) between the anterior face 86 and the posterior face 88 to form an included angle in the range of approximately 50–70 degrees, preferably 60 degrees, in the final hydrated state. For example, as shown in FIG. 4A, each of the opposing end walls 94 forms an angle in the range of approximately 115–125 degrees, preferably 120 degrees, with the anterior face 86; and an angle in the range of approximately 55–65 degrees, preferably 60 degrees with the posterior face 88. It should be recognized that other angles, either greater or smaller, are also acceptable. Additionally, the opposing end walls 94 need not be symmetrical.

With reference to FIG. 4B, the reverse angle prosthetic spinal disc nucleus 80 also tapers in height (z-axis in FIG. 4B) from the anterior face 86 to the posterior face 88. In a preferred embodiment, the prosthetic spinal disc nucleus 80 tapers in height to form an included angle in the range of approximately 2–10 degrees, preferably 6 degrees. For example, the superior face 90 forms an angle in the range of approximately 85–89 degrees with the anterior face 86; and an angle in the range of approximately 91–95 degrees with the posterior face 88. Other dimensions are acceptable, and the superior face 90 and the inferior face 92 need not be symmetrical.

Similar to previous embodiments, the reverse angle prosthetic spinal disc nucleus 80, and in particular the hydrogel core 82, is preferably conditioned prior to implant. Further, radiopaque wires 98 are preferably disposed within the hydrogel core 82. The closures 96 are formed to support and conform to the opposing side walls 94. In other words, each of the closures 96 extend generally parallel to the respective one of the opposing side walls 94, as shown in FIG. 4A. Following conditioning, the hydrogel core 82 is flattened and has a known load-bearing ability, depicted graphically in FIG. 2.

In one preferred embodiment, the reverse angle prosthetic spinal disc nucleus 80, in a final hydrated form, has an overall length in the range of approximately 23–33 millimeters, preferably 28 millimeters. Notably, the overall "length" includes the closures 96 otherwise shown in FIG. 4. Because, as described in greater detail below, the closures 96 do not contact or otherwise interact with opposing end plates of the disc space, the effective working length of the reverse angle prosthetic spinal disc nucleus 80 is the length of the hydrogel core 82, as constrained by the constraining jacket 84, in the hydrated state. With this in mind, the maximum working (or posterior face) length is in the range of approximately 18–22 millimeters, whereas the minimum working (or anterior face) length is in the range of approximately 12–15 millimeters. The reverse angle prosthetic spinal disc nucleus 80 has, in a final hydrated form, a maximum working (or anterior face) height in the range of approximately 6–14 millimeters; a minimum working (or posterior face) height in the range of approximately 5–12 millimeters, and a width in the range of 10–14 millimeters. In one specific example, relating to an average sized disc space, the reverse angle prosthetic spinal disc nucleus 80 preferably has an overall length of 28 millimeters, a minimum working height of 8.5 millimeters, a maximum working height of 10 millimeters, a width of 12.5 millimeters, a maximum working length of 20.5 millimeters and a minimum working length of 13.5 millimeters. It should be recognized, however, that the above-provided dimensions can vary widely such that the reverse angle prosthetic spinal disc nucleus 80 is properly sized for placement within any individual disc space. Additionally, the height of the reverse angle prosthetic spinal disc nucleus 80 will be greatly reduced when the hydrogel core 82 is in a dehydrated state.

D. Implantation of the Prosthetic Nuclei

Figure 5:
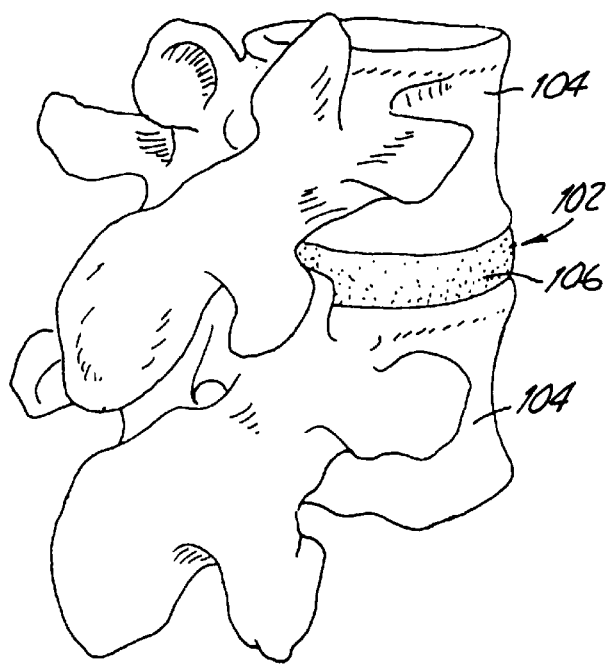
FIG. 5 is an elevated view of a spinal segment including a degenerated discal area.
Figure 6:
FIG. 6 is a posterior view of a human spine showing an opening through an anulus.
Figure 7:
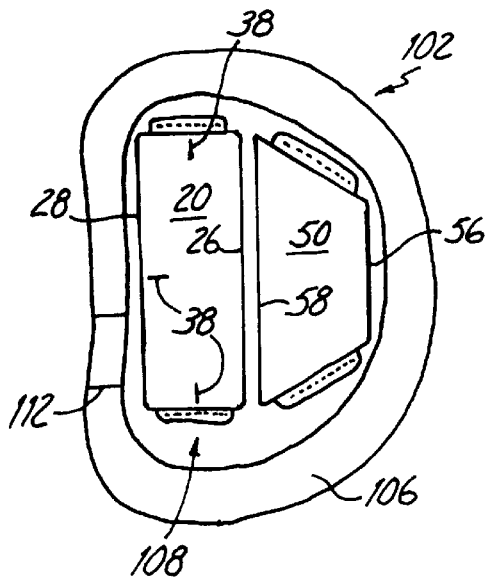
FIG. 7 is a top, sectional view of a human disc space having two prosthetic spinal disc nuclei implanted.

Regardless of which embodiment of the above-described prosthetic spinal disc nuclei 20, 50 or 80 is employed, the preferred method of implantation is identical. For example, FIGS. 5–7 depict implantation of a pair of prosthetic nuclei, including the tapered prosthetic spinal disc nucleus 20 (FIG. 1) and the angled prosthetic spinal disc nucleus 50 (FIG. 3), into a damaged disc space 102. The disc space 102 separates two adjacent vertebrae 104 and includes an anulus 106 and a nucleus region or cavity 108 (shown best in FIG. 7). Proper positioning is achieved by first performing a laminotomy in a targeted lamina area 110. A radial plug (not shown) is removed from a posterior side of the anulus 106, creating a passage 112. The passage 112 has a height less than a height of the anulus 106. Alternatively, a flap can be imparted to create the passage 112. If necessary, excess material is removed from the nucleus cavity 108 to create room for the prosthetic spinal disc nuclei 20, 50. Although in this example a single passage 112 is illustrated and discussed, a pair of passages may alternatively be used.

The tapered prosthetic spinal disc nucleus 20 and the angled prosthetic spinal disc nucleus 50 are then implanted into the nucleus cavity 108 via the passage 112, as shown in FIG. 7. In certain situations, it may be desirable to slightly separate the vertebrae 104 adjacent the damaged disc space 102 to facilitate insertion of the prosthetic spinal disc nuclei 20, 50. With this approach, a pair of passages 112 through the anulus 106 is required. An inflatable jack (not shown) is inserted through one of the passages 112 and inflated to jack apart the adjacent vertebrae 104 (FIG. 6). Once separation sufficient to insert the tapered prosthetic spinal disc nucleus 20 is achieved, the tapered prosthetic spinal disc nucleus 20 is inserted through the passage 112 not occupied by the jack. The jack is deflated and removed, and the angled prosthetic spinal disc nucleus 50 is placed through one of the passages 112. As shown in FIG. 7, following insertion, the prosthetic spinal disc nuclei 20, 50 are preferably rotated to extend transversely within the nucleus cavity 108. For example, the tapered prosthetic spinal disc nucleus 20 is orientated such that the posterior face 28 is adjacent a posterior side of the anulus 106. The anterior face 26 of the tapered prosthetic spinal disc nucleus 20 is centrally located within the nucleus cavity 108. Thus, the tapered prosthetic spinal disc nucleus 20 is positioned within a posterior area or compartment of the nucleus cavity 108. Notably, the radiopaque wires 38 define an orientation and location (via x-ray) of the tapered prosthetic spinal disc nucleus 20 within the nucleus cavity 108. Further, in the event that there is reoccurrence of pain following implant, the radiopaque wires 38 will aid in diagnosis, indicating whether the prosthesis 20 has been displaced from the nucleus cavity 20.

The angled prosthetic spinal disc nucleus 50 is positioned such that the anterior face 56 is adjacent an anterior side of the anulus 106. The posterior face 58, conversely, is centrally located within the nucleus cavity 108. Thus, the angled prosthetic spinal disc nucleus 50 is positioned within a general anterior area or compartment of the nucleus cavity 108. As shown by FIG. 7, then, the tapered prosthetic spinal disc nucleus 20 and the angled prosthetic spinal disc nucleus 50 are sized and orientated to generally conform to the transverse geometry of the nucleus cavity 108. It should be recognized, however, that orientation and selection of prosthetic spinal disc nuclei can and will vary depending upon an individual disc space. For example, the reverse angle prosthetic spinal disc nucleus 80 (FIG. 4) may be used instead of the tapered prosthetic spinal disc nucleus 20 or the angled prosthetic spinal disc nucleus 50. Further, the particular prosthetic spinal disc nucleus 20, 50 or 80 employed may be rotated 180 degrees. Thus, for example, the angled prosthetic spinal disc nucleus 50 may be positioned such that the anterior face 56 is adjacent the posterior side of the anulus 106, whereas the posterior face 58 is centrally located within the nucleus cavity 108. In other words, for example, the angled prosthetic spinal disc nucleus 50 may be positioned at the posterior area or compartment of the nucleus cavity 108. Therefore, any combination, location and orientation of the prosthetic spinal disc nuclei 20, 50 and 80 disclosed can be used.

Figure 8:
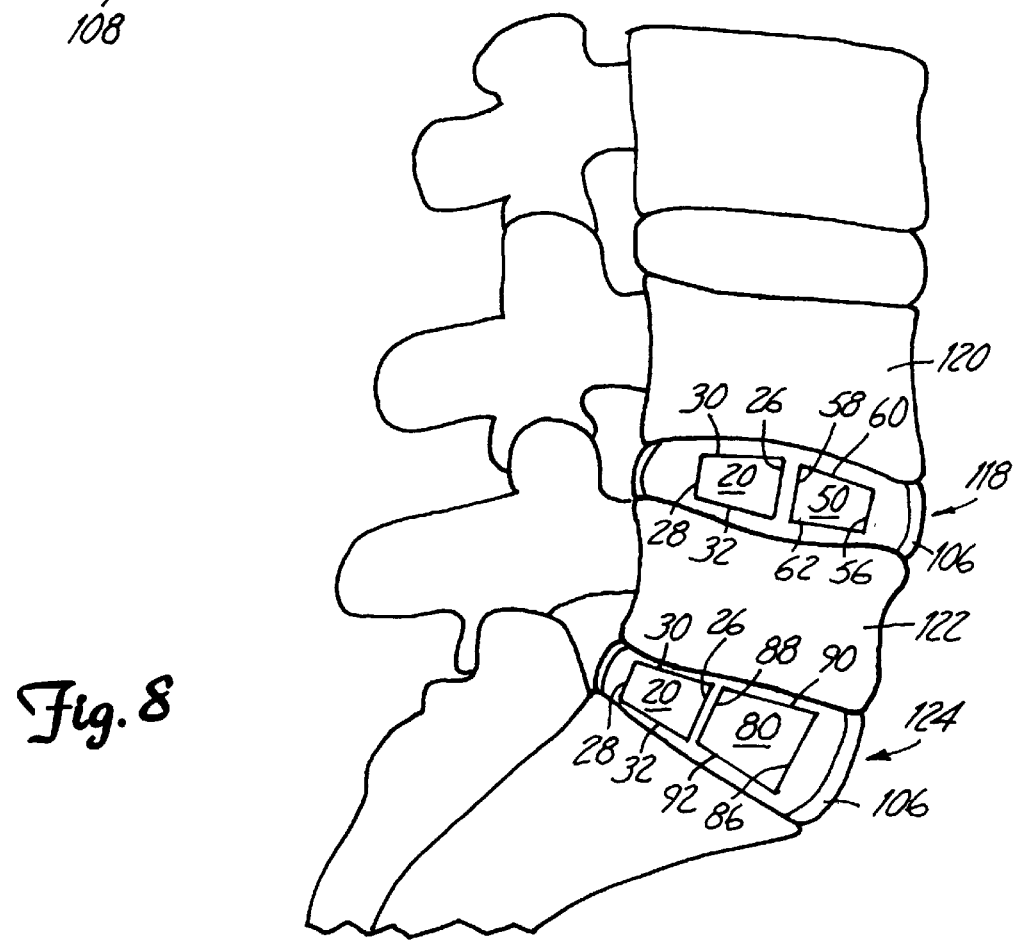
FIG. 8 is a lateral, sectional view of a human spine having prosthetic spinal disc nuclei implanted between the L4 and L5 vertebrae and the L5 and S1 vertebrae.

The pre-formed shape of the prosthetic spinal disc nuclei 20, 50 and 80 account for not only the variation in transverse geometry of the nucleus cavity 108, but also for variations in disc height. As shown in FIG. 8, for example, the prosthetic spinal disc nuclei 20, 50 or 80 can be selected according to the geometric variation in height of a disc space. In this regard, two of the prosthetic spinal disc nuclei 20, 50 are shown as being implanted in a disc space 118 between an L4 vertebrae 120 and an L5 vertebrae 122. The tapered prosthetic spinal disc nucleus 20 is positioned such that the posterior face 28 is adjacent a posterior side of the anulus 106 (or within the posterior area or compartment). Due to the preferred wedge shape, the tapered prosthetic spinal disc nucleus 20 increases in height to the anterior face 26. This wedge shape generally matches the anatomical shape of the posterior side of the L4-L5 disc space 118. Conversely, the angled prosthetic spinal disc nucleus 50 is positioned such that the anterior face 56 is adjacent an anterior side of the disc space 118, whereas the posterior face 58 is centrally located. Once again, the angled prosthetic spinal disc nucleus 50 is wedge-shaped in a final hydrated form, increasing in height from the anterior face 56 to the posterior face 58, generally conforming to an anatomical shape of the anterior side of the L4-L5 disc space 118.

As previously mentioned, the reverse angle prosthetic spinal disc nucleus 80 can be used within a disc space as well. For example, with reference again to FIG. 8, a disc space 124 between the L5 vertebrae 126 and a S1 vertebrae 128 is shown as having one of the tapered prosthetic spinal disc nucleus 20 and one of the reverse angle prosthetic spinal disc nucleus 80 implanted. In this regard, the prosthetic spinal disc nuclei 20, 80 are selected to reflect the geometry of the particular disc space. Thus, the tapered prosthetic spinal disc nucleus 20 is orientated such that the posterior face 28 is adjacent a posterior side of the disc space 124. Conversely, the anterior face 86 of the reverse angle prosthetic spinal disc nucleus 80 is positioned adjacent an anterior side of the disc space 124.

FIG. 8 illustrates three advantages provided by the wedge shape of the prosthetic spinal disc nuclei 20, 50 and 80. First, when attempting to position one of the prosthetic nuclei 20, 50 or 80 adjacent an anterior side of the disc space (such as the L4-L5 disc space 118 in FIG. 8) via a posterior implantation approach, the wedge shape facilitates complete insertion. Because the wedge shape generally matches the decrease in height of the anterior side of the disc space 118, as the prosthesis 20, 50 or 80 is forced anteriorly, the prosthesis 20, 50 or 80 literally acts as a wedge, prying apart the adjacent vertebrae. Thus, it is possible to locate the prosthesis 20, 50 or 80 very near the anterior side of the anulus 106. Second, the wedge shape provides an increased area of contact between superior and/or inferior faces (30, 32; 60, 62; and 90, 92, respectively) and end plates of the disc space 118 or 124. Thus, the stress distribution across the superior (30, 60 or 90) and inferior (32, 62 or 92) faces is relatively uniform. Finally, the wedge-shape nature of the various prosthetic spinal disc nuclei 20, 50, 80 described above provides a natural resistance to retropulsion. In particular, axial loads placed upon the spinal tract force the prosthetic spinal disc nuclei 20, 50 or 80 toward a central portion of the disc space (118 or 124). In other words, due to the angular orientation of the respective superior (30, 60 or 90) and inferior (32, 62 or 92) faces, the normal component of an axial load on the spine will effectively force the prosthetic spinal disc nuclei 20, 50 or 80 centrally within the disc space (118 or 124), thereby preventing undesirable migration.

Figure 9:
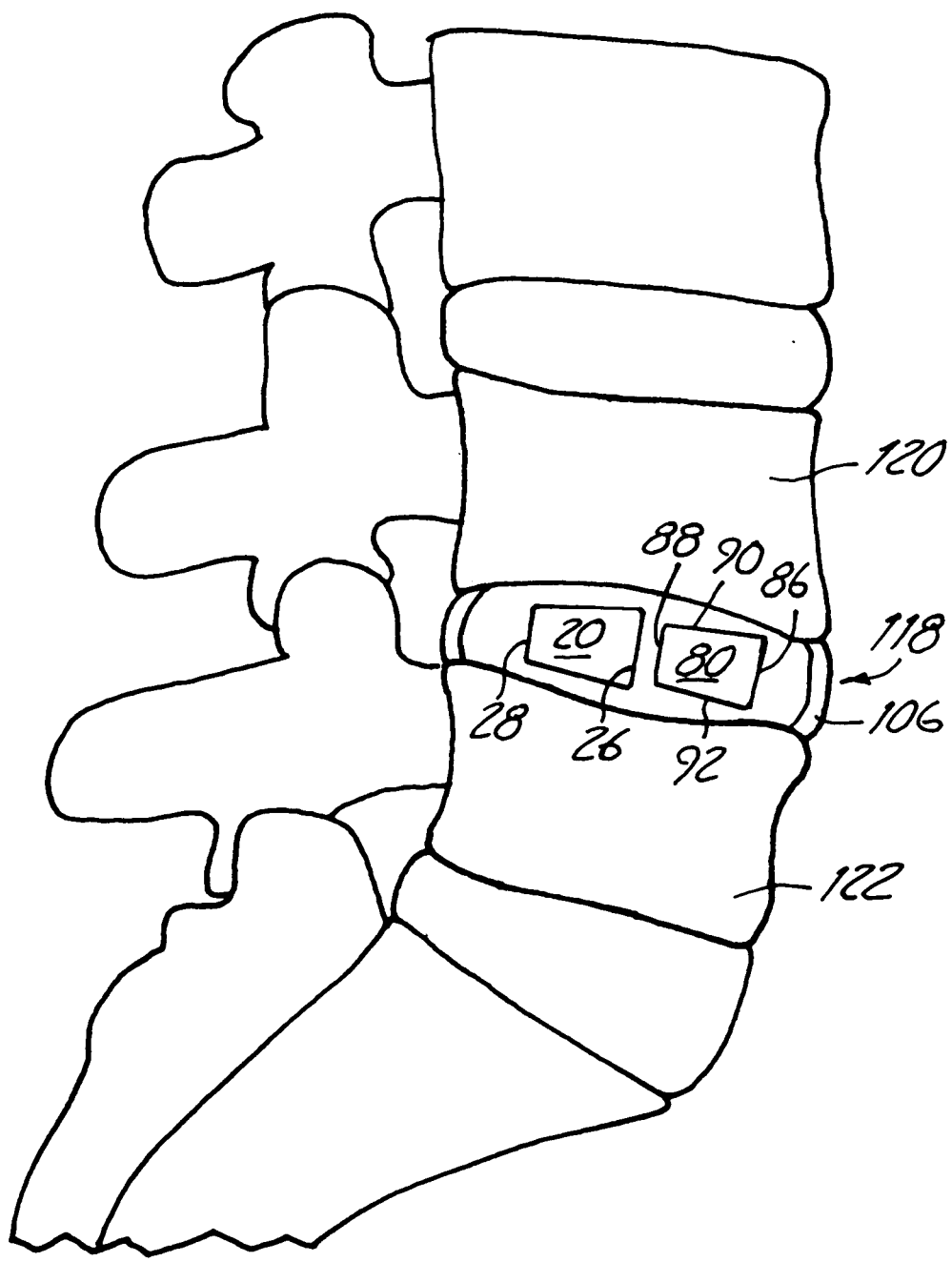
FIG. 9 is a lateral, sectional view of a human spine having a prosthetic spinal disc nuclei implanted between the L4 and L5 vertebrae.

As previously described, multiple combinations, locations and orientations of the prosthetic spinal disc nuclei 20, 50 or 80 are available, depending upon the needs of a particular disc space. Thus, while FIG. 8 has shown the angled prosthetic spinal disc nucleus 50 as being orientated adjacent the anterior side of the L4-L5 disc space 118 such that the height of the prosthesis 50 generally follows the increase in disc space height from the anterior side, other orientations are available. In fact, it has been observed that in some cases, it is advantageous for the prosthetic spinal disc nucleus 20, 50 or 80 to oppose the natural change in height of the disc space 118 at the anterior side. For example, FIG. 9 depicts the reverse angle prosthetic spinal disc nucleus 80 implanted adjacent the anterior side of the L4-L5 disc space 118. More particularly, the anterior face 86 is adjacent the anterior side of the disc space 118, whereas the posterior face 88 is centrally located. It will be recalled that the reverse angle prosthetic spinal disc nucleus 80, in final hydrated form, decreases in height from the anterior face 86 to the posterior face 88. Conversely, the disc space 118 increases in height from the anterior side. FIG. 9 also shows the tapered prosthetic spinal disc nucleus 20 implanted adjacent the posterior side of the disc space 118.

The above-described orientation resists migration of the reverse angle prosthetic spinal disc nucleus 80 and the tapered prosthetic spinal disc nucleus 20. For example, when the spine is subjected to a forward bending movement, opposing end plates of the disc space 118 will pivot toward one another at the anterior side, imparting a force on the superior and inferior faces 90, 92 of the reverse angle prosthetic spinal disc nucleus 80. Because the reverse angle prosthetic spinal disc nucleus 80 increases in height toward the anterior side of the disc space 118, the force generated by the end plates is transposed by the angular shape of the prosthesis 80 into an anterior movement. If the reverse angle prosthetic spinal disc nucleus 80 were positioned so as to decrease in height from the anterior side of the disc space 118 (or if the angled prosthetic spinal disc nucleus were employed as shown in FIG. 8), the bending force might otherwise force the reverse angle prosthetic spinal disc nucleus 80 to move significantly toward the posterior side of the disc space 118, in turn forcing the tapered prosthetic spinal disc nucleus 20 through the opening (not shown) in the anulus 106.

E. Function of the Prosthetic Nuclei

Following implantation, each of the prosthetic spinal disc nuclei 20, 50 or 80 functions as an intervertebral spacer and a cushion, and restores the normal fluid pumping action of the disc space 102 (FIG. 7). Function of the prosthetic nuclei is described below with reference to the tapered prosthetic spinal disc nucleus 20 of FIGS. 1–1B. It should be understood, however, that the angled prosthetic spinal disc nucleus 50 and the reverse angle prosthetic spinal disc nucleus 80 function in an identical manner. Following implant, the hydrogel core 22 imbibes fluids. In this regard, the constraining jacket 24 has sufficient flexibility to allow the hydrogel core 22 to expand. However, the strength and flexibility characteristics of the material used for the constraining jacket 24 are such that the general shape of the hydrogel core 22 will always be maintained. As the hydrogel core 22 hydrates, its volume increases significantly. Due to the preshaping of the hydrogel core 22, the hydrogel core 22 will expand in a general wedge shape. Because the constraining jacket 24 is flexible, it will conform to the shape of the hydrogel core, as shown in FIG. 1. At a certain, predetermined hydration point, the hydrogel core 22 reaches a horizontal expansion limit (x-y plane of FIG. 1A) of the constraining jacket 24, which becomes tight. The constraining jacket 24 has a relatively fixed maximum volume so that the constraining jacket 24 forces the hydrogel core 22 to increase mainly in height (z-axis in FIG. 1B) as more fluids are imbibed. In other words, once the hydrogel core 22 expands to the length (y-axis in FIG. 1A) and width (x-axis in FIGS. 1A and 1B) limits of the constraining jacket 24, the constraining jacket 24 forces further expansion to occur solely in height (z-axis in FIG. 1B). Thus, the constraining jacket 24 works in concert with the hydrogel core 22 to control expansion of the prosthetic spinal disc nucleus 20 after implant. With reference to the implanted position of the prosthetic spinal disc nucleus 20 shown in FIG. 8, this controlled swelling pushes apart or further separates the vertebrae 120, 122 adjacent the disc space 108, as would a normal nucleus. Importantly, the limitation on expansion of the hydrogel core 22 occurs independent of the anulus 106. In other words, the constraining jacket 24 prevents the hydrogel core 22 from expanding to a point at which it would engage and conform to an inner surface of the anulus 106. Once hydrated, the prosthetic spinal disc nucleus 20 will still have a wedge-shaped cross-section, but will be more circular than prior to hydration. The prosthetic spinal disc nucleus 20 will not expand to a completely circular cross-section due to the forces imparted by the vertebral end plates, conditioning of the hydrogel core 22 prior to implant, and the volume limits of the constraining jacket 24.

Following implant and hydration, the prosthetic spinal disc nucleus 20 will deform and reform in response to the placement and removal of loads on the disc space 118 (FIG. 8). The prosthetic spinal disc nucleus 20 flattens in response to placement of physiological loads on the spine, thus assuming a more flattened shape, and acts as a cushion against various loads placed upon it. As these loads are decreased (e.g., when the patient reclines), the hydrogel core 22 reforms back in a predetermined fashion to its original shape, due to the conditioning process described above. To prevent the hydrogel core 22 from escaping, the constraining jacket 24 preferably has a burst strength that is greater than the swelling pressure of the hydrogel core 22 when fully hydrated.

The prosthetic spinal disc nucleus 20 also restores the natural fluid pumping action of the disc space. This relationship is best described with reference to FIG. 7, which depicts the tapered prosthetic spinal disc nucleus 20 and the angled prosthetic spinal disc nucleus 50 implanted within the nucleus cavity 108 of the disc space 102. The hydrated prosthetic spinal disc nuclei 20, 50 occupy a certain percentage, but not all of, the nucleus cavity 108. As loads upon the disc space 102 increase, the prosthetic spinal disc nuclei 20, 50 cushion the vertebral end plates (not shown) and slowly deform. As a result, the volume within the nucleus cavity 108 decreases. Notably, because the prosthetic spinal disc nuclei 20, 50 do not occupy the entire nucleus cavity 108, there is room for the prosthetic spinal disc nuclei 20, 50 to deform, and the reduction in volume of the nucleus cavity 108 is allowed to take place as would otherwise occur with a normal nucleus. In this regard, the respective hydrogel cores 22, 52 (FIGS. 1 and 3) will flatten or deform as a whole, but not decrease in volume in response to the load so that the prosthetic spinal disc nuclei 20, 50 now occupy a larger percentage of the nucleus cavity 108. As a result of the reduction in space, fluids otherwise found within the nucleus cavity 108 are forced out of the disc space 102, thus flushing out the accumulated acids or autotoxins contained therein.

Conversely, when the load is removed or decreased, the prosthetic spinal disc nuclei 20, 50 reform to a more circular (but wedge-shaped) cross-sectional shape. This entails an increase in the vertical direction (relative to the spine in an upright position), causing the vertebral end plates (not shown) to separate, creating an increased volume in the nucleus cavity 108. It will be remembered that the respective hydrogel cores 22, 52 (FIGS. 1 and 3) do not increase in volume, but simply reform. As a result, bodily fluid, containing beneficial nutrients, fills the now-increased volume of the nucleus cavity 108, revitalizing the overall disc space 102. Thus, the prosthetic spinal disc nuclei 20, 50 or 80 act in concert with the natural disc space 102 to restore the natural pumping action of the disc space.

Notably, the prosthetic spinal disc nucleus 20, 50 or 80 of the present invention independently absorbs the force/pressure placed upon the disc space 102. Thus, the anulus 106 is not required to support the force/pressure generated by swelling of the hydrogel core 22, 52 or 82 during hydration. The anulus 106 does not provide any circumferential support to the prosthetic spinal disc nucleus 20, 50 or 80.

The prosthetic spinal disc nucleus of the present invention: (a) restores the height of the damaged disc space; (b) restores and tightens the natural anulus to stop further degeneration and permit its healing; (c) restores the normal load-unload cycling and thus flushes out toxic by-products, bringing in fresh nutrients to the disc space; (d) allows a near-normal range of motion; (e) relieves the movement-induced discogenic pain of the vertebral segment; and (f)

allows the use of a minimal, posterior surgical procedure that provides both cost and medical benefits. In short, the prosthetic spinal disc nucleus of the present invention has the ability to elevate the disc space from the inside, as does the normal, highly hygroscopic nucleus. It will tighten the ligamentous anulus and therefore promote the health and repairability of anular fibers. Beyond these functions, the prosthetic spinal disc nucleus of the present invention generally corresponds to the anatomical geometry of the disc space. In particular, the prosthetic spinal disc nucleus of the present invention accounts for variations in height and diameter of the disc space. The device of the present invention can be implanted with a high degree certainty that the required dimensions presented by the damaged disc space will be maintained following insertion.

Although the present invention has been described with reference to preferred embodiments, workers skilled in the art will recognize that changes may be made in form and detail without departing from the spirit and scope of the invention. For example, other methods of sealing the ends of the constraining jacket exist such as heat, ultrasound, crimp ring seals or spin entanglement. Additionally, more than a single layer of material may be used to maintain the integrity of the hydrogel core. In other words, a plurality of jackets can surround the hydrogel core.

The hydrogel itself can have an outer "skin" formed by ion implantation which causes outer layer cross linking and functions as the constraining jacket or as an interposed membrane between the gel mass and the constraining jacket. Alternatively, expansion and contraction of the hydrogel core can be achieved via the use of a hydrogel that readily expels fluid. Further, other means exist for limiting expansion and contraction in the height of the hydrogel core without the use of a separate jacket. For example, a truss can be embedded along the sides of the hydrogel core.

While the prosthetic spinal disc nucleus has been described as preferably including three radiopaque wires, any number of wires can be used. Alternatively, the hydrogel core may be formulated to include a radiopaque characteristic. Even further, because the prosthetic spinal disc nucleus will function equally as well without any radiopacity, the radiopaque wires can be eliminated entirely.

Finally, the prosthetic spinal disc nucleus has been described as being formed to assume a general wedge-shape (for each of the tapered, angled and reverse angle embodiments) in a dehydrated and hydrated state. In this regard, for each embodiment, certain preferred dimensions have been provided for the prosthetic spinal disc nucleus in a final hydrated state. In other words, the preferred dimensions relate to the hydrogel core being hydrated to the limits of the constraining jacket. While the prosthetic spinal disc nucleus preferably maintains the described wedge shape in a dehydrated state as well, this is not a required feature. Instead, the hydrogel core can be forced to a wide variety of shapes during the final dehydration step. For example, the hydrogel core may be rendered flat (as opposed to wedge-shaped) to facilitate implant. Regardless of the dehydrated shape, the hydrogel core will expand to the desired wedge shape upon hydration due to shape memory and conditioning of the hydrogel core.

What is claimed:

1. A prosthetic spinal disc nucleus for implantation into a nucleus cavity of a spinal disc, the nucleus cavity defined by an opposing pair of vertebral bodies and an anulus, the prosthetic spinal disc nucleus comprising:

a formed hydrogel core configured to expand from a dehydrated state to a hydrated state, the hydrogel core being wedge-shaped prior to implant in at least the hydrated state; and a constraining jacket surrounding the hydrogel core, the constraining jacket being flexible but substantially inelastic, and having a generally fixed maximum volume less than a volume of a nucleus cavity such that the constraining jacket is configured to prevent the hydrogel core from conforming to an anulus upon hydration.

2. The prosthetic spinal disc nucleus of claim 1, wherein the prosthetic spinal disc nucleus defines an anterior face and a posterior face, the prosthetic spinal disc nucleus tapering between the anterior face and the posterior face in at least the hydrated state.

3. The prosthetic spinal disc nucleus of claim 2, wherein the prosthetic spinal disc nucleus defines a height corresponding generally to a height of a spinal disc, the height of the prosthetic spinal disc nucleus increasing from the anterior face to the posterior face.

4. The prosthetic spinal disc nucleus of claim 2, wherein the prosthetic spinal disc nucleus defines a height corresponding generally to a height of a spinal disc, the height of the prosthetic spinal disc nucleus decreasing from the anterior face to the posterior face.

5. The prosthetic spinal disc nucleus of claim 2, wherein the prosthetic spinal disc nucleus defines a length corresponding generally to a transverse plane of a spinal disc, the length of the prosthetic spinal disc nucleus increasing from the anterior face to the posterior face.

6. The prosthetic spinal disc nucleus of claim 2, wherein the prosthetic spinal disc nucleus defines a length corresponding generally to a transverse plane of a spinal disc, the length of the prosthetic spinal disc nucleus decreasing from the anterior face to the posterior face.

7. The prosthetic spinal disc nucleus of claim 2, wherein the hydrogel core defines the anterior face and the posterior face, the hydrogel core configured such that in the hydrated state, the hydrogel core tapers in height to form an included angle in the range of approximately 2–10 degrees.

8. The prosthetic spinal disc nucleus of claim 2, wherein the hydrogel core defines the anterior face and the posterior face, and further defines opposing superior and inferior faces extending between the anterior face and the posterior face, the hydrogel core configured such that the opposing superior and inferior faces are substantially rectangular in the hydrated state.

9. The prosthetic spinal disc nucleus of claim 2, wherein the hydrogel core defines the anterior face and the posterior face, and further defines opposing superior and inferior faces extending between the anterior face and the posterior face, the hydrogel core configured such that the opposing superior and inferior faces are substantially trapezoidal in the hydrated state.

10. The prosthetic spinal disc nucleus of claim 2, wherein the hydrogel core defines the anterior face and the posterior face, and further wherein the hydrogel core is configured such that in the hydrated state, the hydrogel core tapers in length to form an included angle in the range of approximately 50–70 degrees.

11. The prosthetic spinal disc nucleus of claim 1, further including:

a radiopaque wire inserted into the hydrogel core to define a location and orientation of the hydrogel core relative to the nucleus cavity.

12. The prosthetic spinal disc nucleus of claim 1, wherein the hydrogel core expands from a dehydrated state to a horizontal limit of the constraining jacket, the constraining jacket configured to direct expansion of the hydrogel core, from the horizontal limit, in a substantially vertical plane.

13. The prosthetic spinal disc nucleus of claim 1, wherein the generally fixed maximum volume of the constraining jacket is greater than a volume of the hydrogel core in the dehydrated state but less than a volume of the hydrogel core in an unconstrained, fully hydrated state.

14. A prosthetic spinal disc nucleus for implantation into a nucleus cavity of a spinal disc, the nucleus cavity defined by an opposing pair of vertebral bodies, forming opposing end plates, and an anulus, the prosthetic spinal disc nucleus comprising:

a hydrogel core configured to expand from a dehydrated state to a hydrated state, the hydrogel core being preshaped to have, prior to implant and in the hydrated state, a tapered height corresponding generally to an anatomical variation in height of a nucleus cavity; and a constraining jacket surrounding the hydrogel core, the constraining jacket having a generally fixed maximum volume less than a volume of a nucleus cavity and being sized to prevent the hydrogel core from conforming to an anulus upon hydration.

15. The prosthetic spinal disc nucleus of claim 14, wherein in the hydrated state, the hydrogel core is configured to form a wedge shape tapering from a high side to a low side, the high side having a height in the range of approximately 4–16 millimeters.

16. The prosthetic spinal disc nucleus of claim 15, wherein the low side has a height in the range of approximately 3–14 millimeters.

17. The prosthetic spinal disc nucleus of claim 14, wherein in the hydrated state, the constraining jacket constrains the hydrogel core to a width in the range of approximately 8–17 millimeters.

18. The prosthetic spinal disc nucleus of claim 14, wherein the hydrogel core defines opposing superior and inferior faces for engaging the opposing end plates, the superior face being rectangular.

19. The prosthetic spinal disc nucleus of claim 14, wherein the hydrogel core defines opposing superior and inferior faces for engaging the opposing end plates, the superior face being substantially trapezoidal.

20. The prosthetic spinal disc nucleus of claim 14, wherein the hydrogel core tapers in height to define an included angle in the range of approximately 2–10 degrees.

21. The prosthetic spinal disc nucleus of claim 14, wherein the hydrogel core is further configured to, in the hydrated state, taper in length, thereby defining an included angle in the range of 50–70 degrees.

22. A method of manufacturing a prosthetic spinal disc nucleus for implantation into a nucleus cavity of a spinal disc, the nucleus cavity defined by an opposing pair of vertebral bodies and an anulus, the method including:

forming a hydrogel core to an approximate wedge shape prior to implant, the hydrogel core being formed to expand from a dehydrated state to a hydrated state;

providing a substantially inelastic constraining jacket;

dehydrating the hydrogel core; and inserting the hydrogel core into the constraining jacket.

23. The method of claim 22, further including:

subjecting the hydrogel core to a series of conditioning loads in a hydrated state.

24. The method of claim 22, wherein the hydrogel core defines an anterior face and a posterior face, and wherein forming a wedge-shaped hydrogel core includes tapering a height of the hydrogel core between the anterior face and the posterior face.

25. The method of claim 24, wherein tapering a height of the hydrogel core between the anterior face and the posterior face includes forming the hydrogel core to have an included angle in the range of approximately 2–10 degrees in the hydrated state.

26. The method of claim 22, wherein the hydrogel core defines an anterior face and a posterior face, and wherein forming a wedge-shaped hydrogel core includes tapering a length of the hydrogel core between the anterior face and the posterior face.

27. The method of claim 26, wherein tapering a length of the hydrogel core between the anterior face and the posterior face includes forming the hydrogel core to have an included angle in the range of approximately 50–70 degrees in the hydrated state.

28. The method of claim 22, further including:

inserting a radiopaque material into the hydrogel core.

29. The method of claim 22, wherein the constraining jacket is formed to have a generally fixed maximum volume that is less than a volume of the nucleus cavity.

* * * * *